United States Patent [19]

Perregaard et al.

[11] Patent Number: 5,444,073
[45] Date of Patent: Aug. 22, 1995

[54] METHOD FOR TREATING MEMORY IMPAIRMENT

[75] Inventors: Jens K. Perregaard, Jaegerspris, Denmark; Brenda Costall, Bradford, United Kingdom

[73] Assignee: H. Lundbeck A/S, Copenhagen-Valby, Denmark

[21] Appl. No.: 115,449

[22] Filed: Sep. 1, 1993

[30] Foreign Application Priority Data

Mar. 1, 1991 [DK] Denmark .............. 0362/91

[51] Int. Cl.⁶ .......................................... A61K 31/445
[52] U.S. Cl. ..................... 514/323; 514/339
[58] Field of Search .............. 514/226.8, 227.2, 228.2, 514/235.8, 252, 253, 254, 316, 318, 323, 333, 339

[56] References Cited

U.S. PATENT DOCUMENTS

| | | | |
|---|---|---|---|
| 4,847,254 | 7/1989 | Boegesoe | 514/256 |
| 4,946,863 | 8/1990 | Boegesoe | 514/447 |

OTHER PUBLICATIONS

Stern et al. "Long Term administration of Oral Physostigmine" Neurology, 38 1837–41 (1988).
Walters, et al. "Cognitive Enhancing Agents" Can. J. Neurol. Sci. 15 249–256 (1988).
Becker et al "Mechanism of Cholinesterase Inhibition" Drug Develop. Res. 12 163–195 (1988).
Appel "Current Neurology" Year Book Medical Publisher, pp. 315–317 (1987).

*Primary Examiner*—Celia Chang
*Attorney, Agent, or Firm*—Darby & Darby

[57] ABSTRACT

A method for treating memory impairment is disclosed. The method comprises administering a therapeutically effective amount of a compound having the formula:

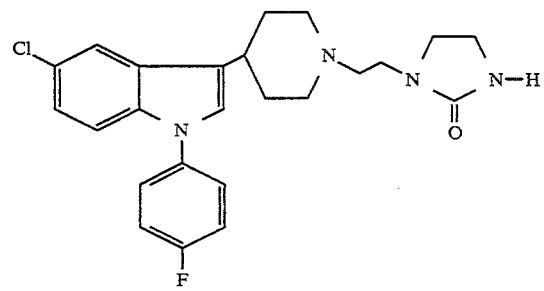

or a pharmaceutically acceptable acid addition salt or prodrug therefor to a patient.

3 Claims, 2 Drawing Sheets

METHOD FOR TREATING MEMORY IMPAIRMENT

FIELD OF THE INVENTION

The present invention relates to the use of compounds belonging to a certain class of 1-aryl-3-(4-piperidyl)-indole derivatives for the treatment of cognitive disorders in man.

BACKGROUND OF THE INVENTION

U.S. Pat. No. 4,710,500 corresponding to EP 200,322 B discloses in general optionally 5-substituted 1-aryl-3-(4-piperidyl)-(I'), 1-aryl-3-(1-piperazinyl)-(II) or 1-aryl-3-(1,2,3,6-tetrahydro-4-pyridyl)indole(III) derivatives having the formulas:

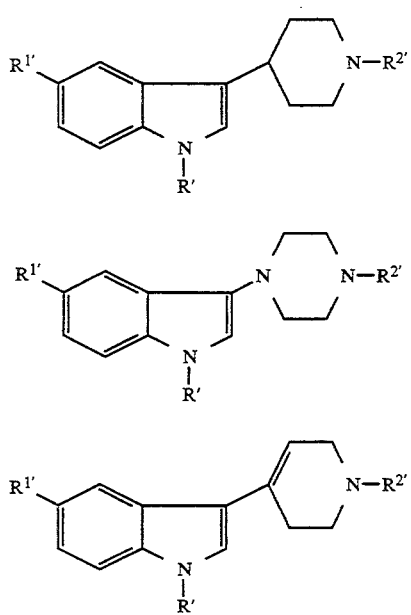

in which formulas R' designates optionally substituted phenyl or a hetero aromatic group, $R^{1'}$ is hydrogen or a substituent such as halogen, alkyl, alkoxy, cyano, nitro, etc, and $R^{2'}$ is hydrogen, alkyl, alkenyl or a certain heterocycle-lower alkyl substituent.

Most of the compounds are shown to be potent and long-lasting dopamine antagonists in vivo, and accordingly to be useful in the treatment of psychoses and all the compounds are proven to be strong serotonin-$S_2$ (5-hydroxytryptamin-2; 5-HT2) receptor antagonists in vivo indicating effects in the treatment of depression and negative symptoms of schizophrenia. The tests used to show blockade of dopaminergic activity in vivo were a catalepsy test and a methylphenidate test, both being at that time regarded as tests for dopaminergic activity. However, at present said two tests are considered also to be a measure of the propensity of an antipsychotic compound to induce extrapyramidal side effects.

Though U.S. Pat. No. 4,710,500 generally comprises the 3-(4-piperidyl) compounds of the Formula I' disclosed above, only five such compounds have been specifically disclosed, i.e. 1-(4-fluorophenyl)-5-methyl-3-(1-methyl-4-piperidyl)-1H-indole, hydrobromide, designated Lu 21-037, 1-(4-fluorophenyl)-3-[1-[2-(2-imidazolidinon-1-yl)ethyl]-1H-indole, designated Lu 23-086, 1-(4-fluorophenyl)-3-[1-[2-(2-pyrrolidinon-1-yl)ethyl]-4-piperidyl]-5-trifluoro-methyl-1H-indole, fumarate, designated Lu 23-158, 1-(4-fluorophenyl)-3-(1-methyl-4-piperidyl)-5-trifluoromethyl-1H-indole, oxalate, designated Lu 21-131, 5-chloro-1-(4-fluorophenyl)-3-[1-[2-(2-imidazolidinon-1-yl)ethyl]-4-piperidyl]-1H-indole, sertindole.

The compound sertindole which is the compound of the above Formula I' wherein $R^{1'}$ is chloro, R' is 4-fluorophenyl and $R^{2'}$ is 2-(2-imidazolidinon-1-yl)ethyl is a known neuroleptic, the neuroleptic activity of which is described in the co-pending U.S. patent application Ser. No. 07/508,240 corresponding to EP 392,959A.

Our copending International Patent Application Publ. No. WO 92/00070 discloses the 3-(4-piperidyl) compounds of the Formula I' as having anxiolytic activity without cataleptic activity and our copending International Patent Application No. PCT/DK91/00291 describes prodrugs of sertindole.

Generally cognitive disorders are an increasing problem among the population due to the increasing mean life age and other factors; so for example the number of Alzheimer's patients are increasing. Generally very little is known about the mechanism of cognition and no effective drugs for the treatment of cognitive disorders are known. Accordingly there is a great demand for drugs effective in the treatment of such disorders.

Surprisingly, it has now been found that certain 1-aryl-3-(4-piperidyl)-indole derivatives having the above general Formula I' in addition to the 5-HT$_2$ receptor antagonistic activity have also cognitive enhancing properties. Furthermore they have been found to be non-cataleptic.

DISCLOSURE OF THE INVENTION

The present invention provides the use of an 1-aryl-3-(4-piperidyl)-indole derivative having the generel formula:

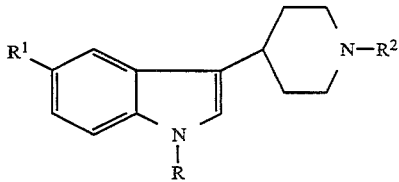

wherein
$R^1$ is hydrogen, halogen, lower alkyl, lower alkoxy, hydroxy, cyano, nitro, lower alkylthio, trifluoromethyl, trifluoromethylthio, lower alkylsulfonyl, amino, lower alkylamino or lower dialkylamino;
R is phenyl optionally substituted with one or more substituents independently selected from the following: halogen, lower alkyl, lower alkoxy, hydroxy, trifluoromethyl, and cyano, or R is 2-thienyl, 3-thienyl, 2-furoyl, 3-furoyl, 2-thiazolyl, 2-oxazolyl, 2-imidazolyl, 2-pyridyl, 3-pyridyl, or 4-pyridyl; and
$R^2$ is hydrogen, cycloalkyl, lower alkyl or lower alkenyl, optionally substituted with one or two hydroxy groups, any hydroxy group present being optionally esterified with an aliphatic carboxylic acid having from two to twentyfour carbon atoms inclusive, or $R^2$ is a group of the Formula IV:

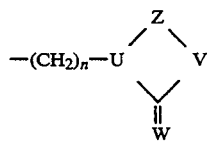

wherein n is an integer from 2–6;

W is oxygen, sulphur or N—R³, wherein R³ is H, lower alkyl or cycloalkyl

U is nitrogen or carbon;

Z is —(CH₂)ₘ—, m being 2 or 3, or Z is —CH═CH— or 1,2-phenylene optionally substituted with halogen or trifluoromethyl, or Z is —COCH₂— or —CSCH₂—;

V is oxygen, sulphur, CH₂, or NR⁴, wherein R⁴ is hydrogen, lower alkyl optionally substituted with one or two hydroxy groups, lower alkenyl or a cycloalkylmethyl group, said cycloalkyl having from three to six carbon atoms inclusive;

or a pharmaceutically acceptable acid addition salt thereof or prodrug therefor for the manufacture of a pharmaceutical preparation for the treatment of cognitive disorders in man.

In another aspect the present invention provides a method for the treatment of cognitive disorders in man comprising the step of administering a therapeutically effective amount of a compound having the Formula I as defined above to a patient in need thereof.

Cognitive disorders to be treated are conditions such as attentional and memory deficits and dementia states occuring for example in senile dementia of the Alzheimer's type, ageing, cerebrovascular deficiency and Parkinson's disease.

The term "lower alkyl" is intended to mean a straight or branched alkyl group having from one to four carbon atoms, such as methyl, ethyl, n-propyl, iso-propyl, n-butyl, sec-butyl, etc. Lower alkoxy, lower alkylthio, lower alkylsulfonyl, lower alkylamino and lower dialkylamino similarly designate such groups wherein the alkyl moiety is a lower alkyl group as defined above.

The term cycloalkyl designates a carbocyclic ring having 3–8 carbon atoms inclusive.

Lower alkenyl is intended to mean an alkenyl group containing from 2 to 4 carbon atoms, for example ethenyl, 1-propenyl, 2-butenyl, etc.

The Z-group —COCH₂— or —CSCH₂— may be oriented in either direction in the ring. Some of the compounds of the general Formula I may exist in optical isomers thereof; and the administration of such optical isomers is also embraced by the method of the invention.

The Prodrugs used in the present invention may be conventional esters with available hydroxy groups, or in particular if the compound is a compound of the general Formula I wherein W is oxygen and V is >NR⁴, R⁴′ being hydrogen, the prodrug may be formed by acylating the nitrogenatom of the V group and being accordingly represented by the Formula I Wherein W is oxygen and V is >N—R⁴′ wherein R⁴′ designates a group —A—B, wherein A is selected from CO, CS, or CH₂, and if A is CO or CS, B is selected from the groups consisting of:

i) hydrogen, alkyl, alkenyl, cycloalkyl, cycloalkenyl or cycloalk(en)ylalk(en)yl, optionally substituted with one or two hydroxy groups, or phenyl optionally substituted with one or more substituents selected from the group consisting of halogen, trifluoromethyl, lower alkyl, lower alkoxy, lower alkylthio, acyloxy, or cyano; or ii) QR⁵, wherein Q is O or S and R⁵ is selected from the substituents defined for B under i) above; and iii) NR⁶R⁷, wherein R⁶ and R⁷ independently are selected from the substituents defined for B under i) above;, or R⁶ and R⁷ are combined to form a four to eight membered heterocyclic ring containing from one to three nitrogen atoms and from zero to three oxygen or sulfur atoms; or if A is CH₂, B is selected from the groups consisting of:

iv) a group QR⁵ as defined in ii);

v) a group NR⁶R⁷ as defined in iii); or vi) a group OC(O)R⁸, wherein R⁸ is as defined for B under i).

Although the latter proodrugs are; not esters, they have been found to decompose properly in order to release tile compound of the invention over an desired period of time when administered parenterally as a depote formulation in an apropriate oil, such as peanut oil, sesame oil, cotton seed oil, corn oil, soy bean oil, olive oil, etc. or synthetic esters of fatty acids and glycerol or propylenglycol, e.g. viscoleo ®.

The pharmaceutically acceptable acid addition salts of the compounds used in the invention are salts formed with non-toxic organic or inorganic acids. Exemplary of such organic salts are those with maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic and theophylline acetic acids, as well as the 8-halotheophyllines, for example 8-bromo-theophylline. Exemplary of such inorganic salts are those with hydrochloric, hydrobromic, sulfuric, sulfamic, phosphoric and nitric acids.

The compounds of the Formula I and the pharmaceutically acceptable acid addition salts thereof may be administered in any suitable way, e.g. orally or parenterally, and the compounds may be presented in any suitable form for such administration, e.g. in the form of tablets, capsules, powders, syrups or solutions or dispersions for, injection.

An effective daily dose of a compound of the Formula I or a pharmaceutically acceptable salt thereof is from 1.0 μg/Kg to 1.0 mg/Kg body weight.

The compounds used in the method of the invention have been found to show effects in an in vivo cognition enhancing test in mice, and they have been found not to induce catalepsy or only induce weak catalepsy which is today regarded as indicative of extrapyramidal side effects. It is indeed very surprising that the present compounds are non-cataleptic whereas the compounds of the Formulas II and III of the above U.S. patent have proved to be cataleptic (c.f. the pharmacological data in the following) and the mechanisms behind this are not fully understood. Accordingly the compounds of the present invention are believed to be useful in the treatment of cognitive disorders without causing extrapyramidal side effects.

Certain imidazolyl-pyridoindol and Imidazolyl-azepinoindol compounds known to be selective 5-HT₃ receptor antagonists have been disclosed also to have effects on cognitive disorders, EP patent publication No. 357 415 A2. However the compounds used in the present invention are very different chemical structures without effects on the 5-HT$_3$ receptor in the brain and their mechanism of action in the cognition test used is not known.

DETAILED DESCRIPTION OF THE INVENTION

Figure 1:
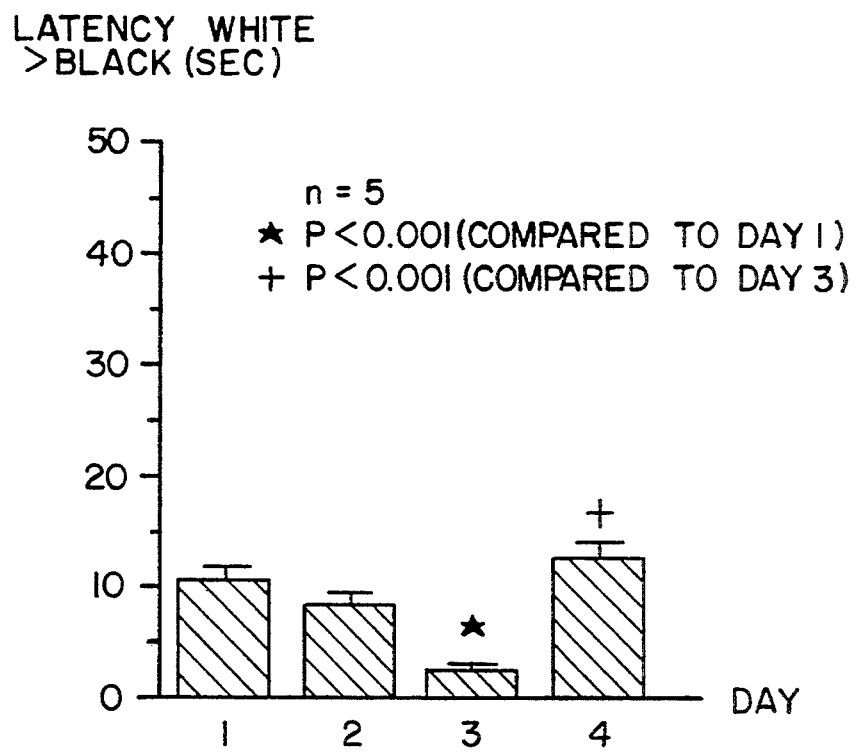
FIG. 1 illustrates the cognitive behaviour-of young adult mice and the effect of scopolamine on the cognitive function in such mice.

In a preferred embodyment of the invention the compound used is a compound of the Formula I as defined in the foregoing wherein R is phenyl substituted in 4 position with fluoro, or R is 2- or 3- thienyl;

R$^1$ is hydrogen, halogen, lower alkyl, lower alkoxy, cyano, trifluoromethyl, or lower alkylsulphonyl;

R$^2$ is a group having the Formula IV as defined in the foregoing wherein n=2-6;

W is oxygen or sulphur;

U is nitrogen;

Z is —(CH$_2$)$_2$—, —(CH$_2$)$_3$—, or —CH=CH—; and

V is oxygen, CH$_2$ or NR$^4$, R$^4$ being hydrogen or lower alkyl;

or a pharmaceutically acceptable acid addition salt thereof or prodrug therefor.

A particularly preferred compound used in the invention is the compound of Formula I wherin R$^1$ is chloro, R is 4-fluorophenyl and R$^2$ is 2-(2-imidazolidinon-1-yl)ethyl known as sertindole.

The compounds of the Formula I used in the invention may be prepared according to methods (b), (c), or (d) described in U.S. Pat. No. 4,710,500. 2-pyrrolidinthiones are prepared from the corresponding lactame derivatives according to litterature methods (Bull.Soc.-Chim. Belg. 87, 223, 229, 299, 525 (1978)) by using Lawesson's reagent or phosphorous pentasulphide at appropriate temperatures. Imidazolidin-2-thion derivatives are prepared by ringclosure reactions from properly substituted ethylendiamines with carbondisulphide, thiophosgen or corresponding thiocarbonyl precursor compounds.

5-Hydroxy substituted indoles are prepared by conventional methods of demethylation of the coresponding methyl ethers. Pyridine hydrochloride or hydrobromide or methionin in methanesulphonic acid is used to split off the methyl group.

The 5-cyano compounds are prepared by substitution of 5-bromo or 5-iodo in the appropriate substituted compounds using CuCN in an aprotic polar solvent such as N,N-dimethylformamide, N-methyl-2-pyrrolidone (NMP) or HMPA at elevated temperatures.

The acid addition salts of the compounds used in the invention are easely prepared by methods well known in the art. The base is reacted with either the calculated amount of organic or inorganic acid in an aqueous miscible solvent, such as acetone or ethanol, with isolation of the salt by concentration and cooling, or an excess of the acid in an aqueous immiscible solvent such as ethyl ether or chloroform with the desired salt separating directly. Of course, these salts may also be prepared by the classical method of double decomposition of appropriate salts.

In addition to the substances specifically mentioned in U.S. Pat. No. 4,710,500, specific examples of compounds used according to the invention are the following compounds which were prepared according to methods (b), (c), or (d) described in U.S. Pat. No. 4,710,500 or from the corresponding lactame derivatives according to litterature methods (Bull.Soc.Chim.-Belg. 87, 223, 229, 299, 525 (1978)) by using Lawesson's reagent or phosphorous pentasulphide at appropriate temperatures:

5-chloro-1-(4-fluorophenyl)-3-[1-(2-hydroxyethyl)-4-piperidyl]-1H-indole, hydrochloride, 1 MP: 266°–269° C.

5-chloro-1-(4-fluorophenyl)-3-[1-[2-(2-oxazolidinon-1-yl)ethyl]-4-piperidyl]-1H-indole, fumarate, 2, MP: 203°–205° C.

5-chloro-1-(4-fluorophenyl)-3-[1-[2-(3-methyl-2-imidazolidinon-1-yl)ethyl]4-piperidyl]-1H-indole, fumarate, 3, MP: 198°–199° C.

5-chloro-1-(4-fluorophenyl)-3-[1-[2-(2-pyrrolidinon-1-yl)ethyl]-4-piperidyl]-1H-indole, fumarate, 4, MP: 209°–211° C.

1-(4-fluorophenyl)-3-[1-[2-(3-methyl-2-imidazolidinon-1-yl)ethyl]-4-piperidyl]-5-trifluoromethyl- 1H-indole, 5, MP: 144°–145° C.

1-(4-fluorophenyl)-3-[1-[2-(2-oxazolidinon- 1-yl)ethyl]-4-piperidyl]-5-triflouro-methyl-1H-indole, fumarate, 6, MP: 212°–213° C.

5-chloro-1-(4-fluorophenyl)-3-[1-[2-(2-pyroolidinthion-1-yl)ethyl]-4-piperidyl]-1H-indole, fumarate, 7, MP: 195°–199° C.

1-(4-fluorophenyl)-3-[1-[2-(2-imidazolidinon-1-yl)ethyl]-4-piperidyl]-5-methyl-sulfonyl-1H-indole, fumarate, 8, MP: 188°–192° C.

5-chloro-1-1-(4-fluorophenyl)-3-[1-[6-(2-pyrolidinon-1-yl)-1-hexyl]-4-piperidyl]-1H-indole,hydrochloride, 9, MP: 123°–128° C.

5-chloro-1 -(4-fluorophenyl)-3-(4-piperidyl)-1H-indole, fumarate, 10, MP: 196°–201 ° C.

1-(4-fluorophenyl)-3-(4-piperidyl)-5-trifluoromethyl-1H-indole, hydrochloride, 11 MP 281–284° C.

1-(4-fluorophenyl)-3-[1-[2-(2-imidazolidinon-1-yl)ethyl]-4-piperidyl]-5-trifluoro-methyl-1H-indole, 12, MP: 169°–171 ° C.

1-(4-fluorophenyl)-3-[1-[6-(2-pyrrolidinon-1-yl)-1-hexyl]-4-piperidyl]-5-trifluoromethyl-1H-indole,oxalate, 13, MP: 85°–87° C.

5-chloro-1-(4-fluorophenyl)-3-[1-[2-[3-(2-propyl)-2-imidazolidinon-1-yl]ethyl]-4-piperidyl]-1H-indole, oxalate, 14, MP: 92°–96° C.

5-fluoro-1-(4-fluorophenyl)-3-(4-piperidyl)-1H-indole, fumarate, 15, MP: 198°–200° C.

5-fluoro-1-(4-fluorophenyl)-3-[1-[2-(2-imidazolidinon-1-yl)ethyl]-4-piperidyl]-1H-indole, oxalate, 16, MP: 188°–190° C.

5-fluoro-1-(4-fluorophenyl)-3-[1-[2-(2-pyrrolidinon-1-yl)ethyl]-4-piperidyl]-1H-indole, fumarate, 17, MP: 178°–180° C.

5-fluoro- 1-(4-fluorophenyl)-3-[1-[2-[3-(2-propyl)-2-imidazolidinon-1H-indole, fumarate, 18, MP: 115°–120° C.

5-chloro-1-(4-fluorophenyl)-3-[1-[5-(2-imidazolidinon-1-yl)-1-pentyl]-4-piperidyl]-1H-indole, oxalate, 19, MP: 145°–147° C.

5-chloro-1-(4-fluorophenyl)-3-[1-[4-(2-imidazolidinon-1-yl)-1-butyl]-4-piperidyl]-1H-indole, oxalate, 20, MP: 178°–179° C.

5-chloro- 1-(4-fluorophenyl)-3-[1-[6-(2-imidazolidinon-1-yl)-1-hexyl]-4-piperidyl]-1H-indole, oxalate, 21, MP: 156°–158° C.

5-chloro-1-(4-fluorophenyl)-3-[1-[2-(hydantoin-2-yl)ethyl]-4-piperidyl]-1H-indole, 22, MP: 174°–176° C.

5-fluoro-1-(4-fluorophenyl)-3-[1-[6-(2-pyrrolidinon-1-yl)-1-hexyl]-4-piperidyl]-1H-indole, 23, oil 1-(4-fluorophenyl)-3-[1-[2-(2-imidazolidinon-1-yl)ethyl]-4-piperidyl]-5-methyl-1H-indole, 24, MP: 187°–189° C.

1-(4-fluorophenyl)-3-[1-[2-[3-(2-propyl)-2-imidazolidinon-1-yl]ethyl]-4-piperidyl]-5-methyl-1H-indole, hydrochloride, hydrate, 25, MP: 214°–215° C.

1-(4-fluorophenyl)-3-[1-[2-(2-pyrrolidinon-1-yl)ethyl]-4-piperidyl]-5-methyl-1H-indole, hydrochloride, hemihydrate, 26, 265°–266° C.

1-(4-fluorophenyl)-3-[1-[2-[3-(2-propyl)-2-imidazolidinon-1-yl]ethyl]-4-piperidyl]-5-trifluoromethyl-1H-indole, 27, MP: 99°–100° C.

3-[1-[2-(2-imidazolidinon-1-yl)ethyl]-4-piperidyl]-1-(3-thienyl)-1H-indole, MP: 139°–140° C.

1-(4-fluorophenyl)-3-[1-[2-(2-imidazolidinon-1-yl)ethyl]-4-piperidyl]-5-methoxy-1H-indole, 29, MP:167° C.

5-fluoro-3-[1-[2-[3-(2-propyl)-2-imidazolidinon-1-yl]ethyl]-4-piperidyl]-1-(3-thienyl)-1H-indole, oxalate, hemihydrate, 30, MP : 95°–97° C.

5-fluoro-3-[1-[2-[3-(2-propyl)-2-imidazolidinon- 1-yl]ethyl]-4-piperidyl]-1-(2-thienyl)-1H-indole, dioxalate, 31, MP: 173°–174° C.

5-bromo-1-(4-fluorophenyl)-3-[1-[2-(2-imidazolidinon-1-yl)ethyl]-4-piperidyl]-1H-indole, 32, MP: 171°–172° C.

1-(4-fluorophenyl)-3-[1-[2-[3-(2-propyl)-2-imidazolidinon-1-yl]ethyl]-4-piperidyl]-1H-indole, hydrochloride, 33, MP :226°–227° C.

5-chloro-1-(4-fluorophenyl)-3-[1-[3-(2-imidazolidinon-1-yl)- 1 -propyl]-4-piperidyl]-1H-indole, fumarate, 34, MP: 203°–205° C.

In the following examples the preparation of an imidazolidin-2-thion derivative and of two derivatives having a hydroxyl and a cyano group, respectively, in the 5-position of the indole ring is shown:

EXAMPLE 1

5-chloro-1-(4-fluorophenyl)-3-[1-[2-(2-imidazolidinthion-1-yl)ethyl]-4-piperidyl]-1H-indole, oxalate, 35, MP: 150° C.

To a solution of 5-chloro-1-(4-fluorophenyl)-3-(4-piperidyl)-1H-indole (25 g)in N-methyl-2-pyrrolidone (150 ml) were added chloroacetonitrile (6 g) and triethylamine (10 ml). The reaction mixture was heated at 60° C. for one hour and subsequently poured onto crushed ice. The precipitated 5-chloro-3-(1-cyanomethyl-4-piperidyl)-1-(4-fluorophenyl)-1H-indole was filtered off and washed with water. Yield 20 g. MP: 170°–172° C.

A solution of the thus isolated cyanomethylderivative (24 g) in dry THF (150 ml) was added dropwise to a previously prepared solution of AlH$_3$ (from 8 g of LiAlH$_4$ and 8 g of AlCl$_3$) in dry diethyl ether (250 ml). The mixture was heated at reflux for one hour and finally hydrolyzed by carefully adding a conc. aqueous solution of NaOH (10 ml) under simultaneous cooling. Inorganic salts were filtered off and were subsequently carefully washed with hot dichloromethane (2×100 ml). the combined organic phases were dried (anh. MgSO$_4$) and finally evaporated leaving 3-[1-(2-aminoethyl)-4-piperidyl]-5-chloro-1-(4-fluorophenyl)-1H-indole (25 g) as an oil.

Without further purification this product (12 g) and triethylamine (4.2 g) were heated in 1,1,1-trichloroethane (100 ml) at 50°–55° C. A solution of chloroacetonitrile (3.6 g) in 1,1,1-trichloroethane (10 ml) were added dropwise during 10 minutes. The mixture was heated for another 4 hours at 50° C. Ethyl acetate (200 ml) was added and the mixture was poured into ice cooled dil. aqueous NaOH solution (400 ml). The organic phase was separated, washed with brine, dried (anh. MgSO$_4$) and the solvents evaporated leaving 5-chloro-3-[1-[2-(N-cyanomethyl)aminoethyl]-4-piperidyl]-1-(4-fluorophenyl)-1H-indole (14 g) as an oil.

The oil thus isolated was dissolved in dry THF (100 ml) and added dropwise to a previously prepared solution of AlH$_3$ (from 6 g of LiAlH$_4$ and 6 g of AlCl$_3$) in dry diethyl ether (200 ml). The mixture was refluxed for one hour and finally hydrolyzed by cautiously adding a conc. aqueous solution of NaOH (8 ml) under simultaneous cooling. Inorganic salts were filtered off and were subsequently washed with hot dichloromethane (2×100 ml). The combined organic phases were dried (anh. MgSO$_4$) and finally evaporated leaving 3-[1-[N-(2-aminoethyl)-2-aminoethyl]-4-piperidyl]-5-chloro-1-(4-fluorophenyl)-1H-indole (8.5 g) as an oil. This oil (4.5 g) was dissolved in 1-pentanol (50 ml) and carbondisulphide (5 ml) was added. After stirring for 2 hours at room temperature the resulting suspension was heated to 140° C. for 1.5 hours. Excess CS$_2$ was flushed away by a gentle stream of N$_2$ gas. Finally most of the 1-pentanol was evaporated at reduced pressure. The remaining oil was purified by column chromatography on silica gel (eluted with ethyl acetate/ethanol/triethylamine—80/20/4). The oxalate salt of the title compound 35 crystallized from acetone. Yield 250 mg. MP: 150° C.

EXAMPLE 2

1-(4-Fluorophenyl)-5-hydroxy-3-[1-[2-(2-imidazolidinon-1-yl)ethyl],4-piperidyl]-1H-indole, 36, MP: 220° C.

Pyridinhydrochloride (60 g) and 1-(4-fluorophenyl)-3-[1-[2-(2-imidazolidinon-1yl)ethyl]-4-piperidyl]-5-methoxy-1H-indole, compound 29 (6 g) were mixed and heated to 180° C. under N$_2$ for 1½ hours. After cooling, water (300 ml) and ethyl acetate (100 ml) were added. By addition of NH$_4$OH solution the pH was adjusted to >9. The organic phase was separated, washed with water (50 ml), dried (anh. MgSO$_4$), and the solvent evaporated leaving the phenolic crude title compound as an oil. Purification by column chromatography on silica gel (eluted with ethyl acetate/dichloromethane/ethanol/triethylamine 60:20:20:5) afforded the title compound 36 as a crystalline material. Yield: 1.9 g. MP: 220° C.

EXAMPLE 3

-Cyano-1-(4-fluorophenyl)-3-[1-[2-(2-imidazolidinon-1-yl)ethyl]-4-piperidyl]-1H-indole, 37, MP: 209° C.

To a solution of 5-bromo1-(4-fluorophenyl)-3-(4-piperidyl)-1H-indole (17 g) in dichloromethane (170 ml) was added a solution of ditert.-butyloxycarbonate (12 g) in dichloromethane (30 ml). After stirring for 30 minutes at room temperature the dichloromethane was evaporated in vacuo. 5-Bromo-3-(1-tert-butyloxycarbonyl-4-piperidyl)-1-(4-fluorophenyl)-1H-indole crystallized from n-heptane. Yield: 14 g. MP: 155° C.

All the crystalline material was dissolved in N-methyl-2-pyrrolidone (75 ml) and CaCN (5 g) was added. The, mixture was heated at 160° C. for 6 hours. The mixture was then poured into a solution of NaCN (10 g) in water (200 ml) and stirred for 20 minutes. Diethyl ether (200 ml) was added. The ether phase was separated, washed with brine (50 ml), dried (anh. $MgSO_4$), and the ether evaporated leaving a mixture of 5-bromo and 5-cyano compounds which were separated by coloumn chromatography on silica gel (eluted with diethyl ether). The 3-(1-tert.butyloxycarbonyl-4-piperidyl)-5-cyano-1-(4-fluorophenyl)-1H-indole was isolated an an oil. Yield: 4.5 g.

The protecting group—tert.butyloxycarbonyl— was splitted off by standard acidic ($CF_3COOH$) decomposition. The thus obtained 5-cyano-1-(4-fluorophenyl)-3-(4-piperidyl)-1H-indole (3.2 g) was dissolved in methyl isobutyl ketone (90 ml). Potassium carbonate (4.5 g), potassium iodide (0.5 g) and 1-(2-chloroethyl)-2-imidazolidinone (2.3 g) were added. The mixture was refluxed for 16 hours. After cooling inorganic salts were filtered Off, and the organic solvent evaporated. Water (100 ml) and ethyl acetate (50 ml) were added. The organic phase was separated, dried (anh. $MgSO_4$), and finally ethyl acetate evaporated leaving the crude title compound as an oil. Purification by column chromatography on silica gel (eluted with ethyl acetate/ethanol/triethylamine 80:20:4) afforded 2.1 g of pure crystalline title compound, 37. MP: 209° C.

PHARMACOLOGY

The compounds used in the invention were tested in accordance with well recognized and reliable test methods. The tests were as follows:

CATALEPSY TEST

Evaluation of catalepsy is made according to Arnt (Eur. J. Pharmacol. 90, 47–55 (1983)). Test compound is given s.c. in different doses. The rat (170–240 g) is placed on a vertical wire mesh (mesh-diameter 12 mm). The rat is considered cataleptic if it remains immobile for more than 15 sec. The maximum number of rats showing catalepsy within the first 6 hours is recorded for each dose group. The results are recorded in fractions and an $ED_{50}$ value is calculated by means of log-probit analysis. The results are shown in table 1.

The following corresponding 1-aryl-3-(1,2,3,6-tetrahydrpyridyl)- or 1-aryl-3(piperazinyl)indole derivatives which are analogues of sertindole and compound No 12, respectively, were included in the test as comparing compounds:

1-(4-Fluorophenyl)-3-[1-[2-(2-imidazolidinon-1-yl)ethyl]-1,2,3,6-tetrahydropyridin-4-yl]-5-trifluoromethyl- 1H-indole (Comp. A):

5-Chloro-1-(4-fluorophenyl)-3-[1-[2-(2-imidazolidinon-1-yl)ethyl]-1,2,3,6-tetrahydropyridin-4-yl]-5-trifluoromethyl-1H-indole (Comp B); and 5-Chloro-1-(4-fluorophenyl)-3-[4-[2-(2-imidazolidinon-1-yl)ethyl]-12,3,6-tetrahydropyridin-4-yl]-5-trifluoromethyl-1H-indole (Comp. C).

TABLE 1

| Compound | Cataleptic Activity ED50(s.c.) (μmol/kg) |
|---|---|
| Sertindole | >98 |
| Comp. No 12 | 38 |
| Comp. No 2 | >18 |
| Comp. No 3 | 31 |
| Comp. No 4 | 23 |
| Comp. No 14 | >69 |
| Comp. No 16 | >78 |

TABLE 1-continued

| Compound | Cataleptic Activity ED50(s.c.) (μmol/kg) |
|---|---|
| Comp. No 24 | >95 |
| Comp. A | 0.49 |
| Comp. B | 2.2 |
| Comp. C | 4.5 |

Further $ED_{50}$ values of corresponding 1-aryl-3-(1,2,3,6-tetrahydro-4-pyridyl)- or 1-aryl-3-(1-piperazinyl)indole derivatives are given in U.S. Pat. No. 4,710,500.

INHIBITION OF SCOPOLAMINE INDUCED MEMORY IMPAIRMENT IN MICE

The test is a test for the effect of a cognition enhancing substance on the latency of a mouse to move from an aversive white brightly illuminated compartment to a less aversive black dimly illuminated compartment on repeated exposure to the test situation and for the antagonizing effect of said substance on the memory impairing substance scopolamine in this test.

Procedure

The test was conducted using an open-top experimental box (45*27*27 cm) two fifths of which was partitioned from the rest, painted black and illuminated with a dim red light (1×60 W). The remainder of the box was painted white and brightly illuminated (60 W) with a white light source. Acces between the two compartments was by means of a 7.5×7.5cm opening located in floor level at the centre of the partition.

The mice were aged male albino (BKW) mice having an age 8–12 month (aged mice) housed in groups of 10 and given free acces to drink and food and kept on a dark/light cycle of 12 hours.

The test was carried out by placing the mice (taken from a dark home environment) in the centre of the white section of the test box. The test period was 5 min. per day. The latency to move from the white to the black section was assed via remote video recording. On day 4 scopolamine (0.25 mg/kg (control group of young mice) or 0.1 mg/kg (aged mice, test group and control group)i.p.b.d.) was given 40 min's prior to testing.

Test compound was given i.p.b.d. before the testing. As control animals young male albino (BKW) mice having an age of 6–8 month and a group of aged male albino (BKW) mice were used.

Data obtained were analysed BY a one-way ANOVA followed by Dunnett's t-test.

Figure 2:
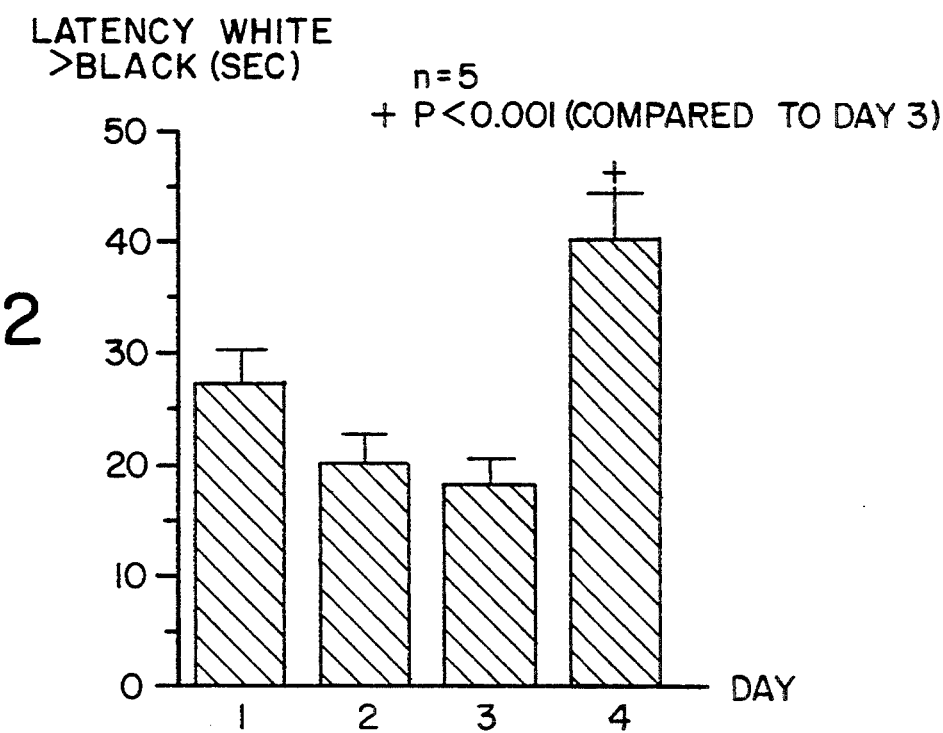
FIG. 2 illustrates the cognitive behaviour of aged mice and the effect of scopolamine on the cognitive function in such mice.
Figure 3:
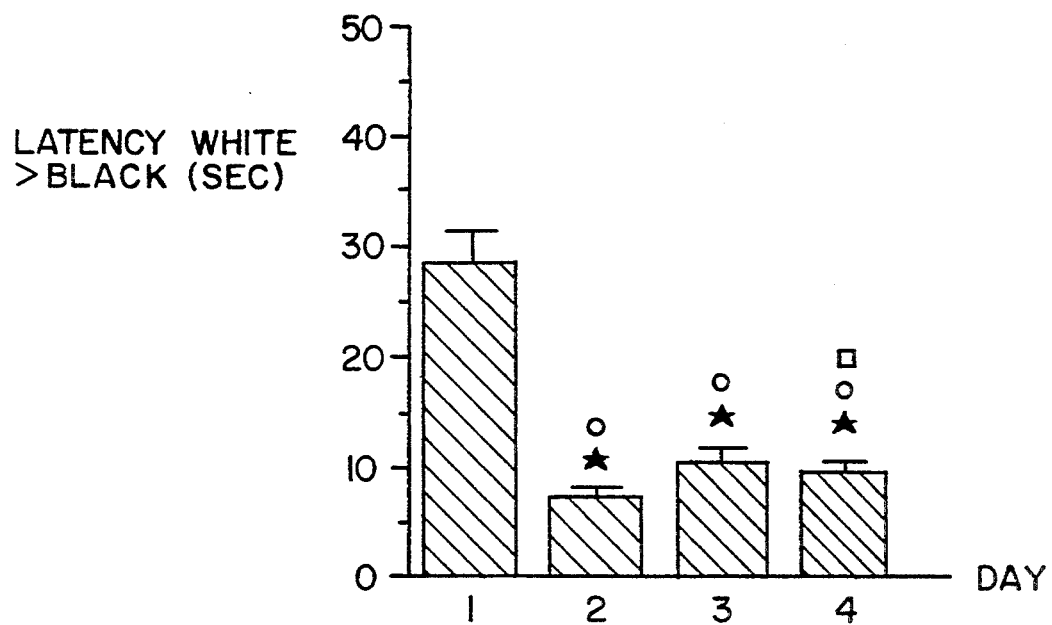
FIG. 3 illustrates the effect of a compound of the invention, i.e. sertindole given j.p.b.d. in a dose of 0.01 ng/kg on the cognitive function in aged mice.

The results are shown graphically in FIG. 3 for one compound according to the invention, i.e. sertindole, administrated in a dose of 0.01 mg/kg. FIGS. 1 and 2 show the results for the control groups.

It appears from table 1 that the compounds of the invention are without or substantially without cataleptic activity and accordinly being lacking the extrapyramidal side effects probably associated with the corresponding known 3-(1,2,3,6-tetrahydro-4pyridyl) and 3-(1-piperazinyl) derivatives.

It is clearly demonstrated in FIG. 1 that the compound according to the invention has a marked cognitive enhancing effect both before and after administration of scopolamine.

FORMULATION EXAMPLES

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting maschine. Examples of adjuvants or diluents comprise: corn starch, potato starch, talcum, magnesium stearate, gelatine, lactose, gums, and the like. Any other adjuvant or additive colourings, aroma, preservatives etc. may be used provided that they are compatible with the active ingredients.

Solutions for injections may be prepared by solving the active ingredient and possible additives in a part of the solvent for injection, preferably sterile water, adjusting the solution to the desired volume, sterilization of the solution and filling in suitable ampules or vials. Any suitable additive conventionally used in the art may be added, such as tonicity agents, preservatives, antioxidants, etc.

Typical examples of recipes for the formulations of the invention are as follows:

| 1) Tablets containing 5 milligrams of sertindole calculated as the free base: | |
|---|---|
| Sertindole | 0.5 mg |
| Lactose | 18 mg |
| Potato starch | 27 mg |
| Saccharose | 58 mg |
| Sorbitol | 3 mg |
| Talcum | 5 mg |
| Gelatine | 2 mg |
| Povidone | 1 mg |
| Magnesium stearate | 0.5 mg |
| 2) Tablets containing 1.0 milligrams of compound No 3 calculated as the free base: | |
| Comp. 3 | 1.0 mg |
| Lactose | 16 mg |
| Potato starch | 45 mg |
| Sacc'harose | 106 mg |
| Sorbitol | 6 mg |
| Talcum | 9 mg |
| Gelatine | 4 mg |
| Povidone | 3 mg |
| Magnesium stearate | 0.6 mg |
| 3) Syrup containing per milliliter: | |
| Comp. 16 | 5.0 mg |
| Sorbitol | 500 mg |
| Tragacanth | 7 mg |
| Glycerol | 50 mg |
| Methyl-paraben | 1 mg |
| Propyl-paraben | 0.1 mg |
| Ethanol | 0.005 ml |
| Water | ad 1 ml |
| 4) Solution for injection containing per milliliter: | |
| Sertindole | 0.2 mg |
| Acetic acid | 17.9 mg |
| Sterile water | ad 1 ml |
| 5) Solution for injection containing per milliliter: | |
| Comp. 3 | 0.5 mg |
| Sorbitol | 42.9 mg |
| Acetic acid | 0.63 mg |
| Sodium hydroxide | 22 mg |
| Sterile water | ad 1 ml |

What is claimed is:

1. A method for treating memory impairment comprising administering a therapeutically effective amount of a compound having the formula:

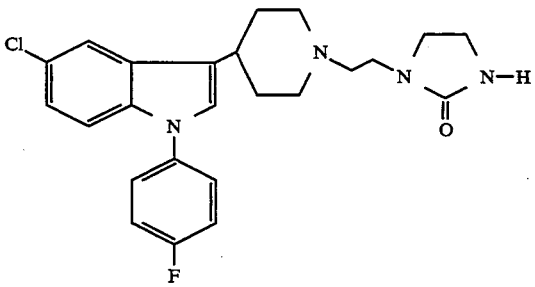

or a pharmaceutically acceptable acid addition salt or prodrug therefor to a patient in need thereof.

2. A method according to claim 1 wherein the memory impairment is caused by a dementia state.

3. A method according to claim 1 wherein the memory impairment is caused by Alzheimer's disease, senile dementia, cerebrovascular deficiency or Parkinson's disease.

* * * * *